(12) United States Patent
Kalinin

(10) Patent No.: US 7,844,414 B2
(45) Date of Patent: Nov. 30, 2010

(54) METHOD OF CALIBRATING TEMPERATURE COMPENSATED SENSORS

(75) Inventor: Victor Alexandrovich Kalinin, Headington (GB)

(73) Assignee: Transense Technologies PLC, Bicester, Oxon (GB)

( * ) Notice: Subject to any disclaimer, the term of this patent is extended or adjusted under 35 U.S.C. 154(b) by 104 days.

(21) Appl. No.: 12/328,479

(22) Filed: Dec. 4, 2008

(65) Prior Publication Data

US 2009/0082985 A1    Mar. 26, 2009

Related U.S. Application Data

(63) Continuation-in-part of application No. 12/035,777, filed on Feb. 22, 2008, now abandoned.

(30) Foreign Application Priority Data

Dec. 12, 2007 (GB) ................................ 0724243.1
Feb. 11, 2008 (GB) ................................ 0802498.6
Jul. 22, 2008 (GB) ................................ 0813420.7

(51) Int. Cl.
*G01D 18/00* (2006.01)

(52) U.S. Cl. ........................... 702/130; 702/85; 702/86; 702/88; 702/99; 702/103; 702/104; 702/127; 702/189; 702/199; 73/1.01; 73/1.82; 73/1.88; 703/2; 703/4; 714/1

(58) Field of Classification Search ................... 702/85, 702/86, 88, 99, 103, 104, 127, 130, 189, 702/199; 73/1.01, 1.82, 1.88; 703/2, 4; 714/1
See application file for complete search history.

(56) References Cited

PUBLICATIONS

Kalinin et al, "Contactless Torque and Temperature Sensor Based on SAW Resonators," IEEE Ultrasonice Symposium, pp. 1490-1493. 2006.*

* cited by examiner

*Primary Examiner*—Sujoy K Kundu
(74) *Attorney, Agent, or Firm*—Keusey & Associates, P.C.

(57) ABSTRACT

A method of calibrating an individual sensor of a particular sensor type whose output varies non-linearly with at least one measured quantity and at least one operating condition. The first step includes producing a set of calibration curves for each sample sensor of the particular sensor type. The resulting sets of calibration curves are then averaged and the results used to produce a generic calibration surface for the particular sensor type showing its variation. Individual calibration measurements are then taken for a number of different values of the measured quantity at a small number of discrete values. The individual calibration readings are then used to map the generic calibration surface to the individual calibration measurements of the individual sensor.

13 Claims, 2 Drawing Sheets

METHOD OF CALIBRATING TEMPERATURE COMPENSATED SENSORS

This application is a continuation-in-part of U.S. patent application Ser. No. 12/035,777, entitled "Method of Calibrating Temperature Compensated Sensors," filed Feb. 22, 2008 now abandoned, by Kalnin, which is still and which is incorporated by reference herein.

BACKGROUND OF THE INVENTION

1. Field of the Invention

The present application relates to methods for calibrating sensors for measuring physical parameters in which reading of the sensor varies depending upon conditions such as temperature, so that compensation of the reading from the sensor must be done in order to obtain an accurate value for the measured parameter, and more particularly to calibrating such sensors whose output depends non-linearly on a measured quantity (torque) and on an operating condition (temperature).

2. The Prior Art

The application deals with physical sensors for measuring such quantities as mechanical strain, force, acceleration, pressure, torque, electric and magnetic fields, power, etc. Very often, the sensor reading varies with surrounding conditions, in particular on the ambient temperature, and the only way to compensate this dependence is to measure the temperature along with the physical quantity of interest. In the approach known in the prior art, the sensor is calibrated within the entire working range of temperatures and then the temperature compensated reading is obtained as a result of processing of the information provided by the sensing element in a microprocessor on the basis of a certain calibration model of the sensor.

More particularly, if the aim is to measure the physical quantity M within the range of temperatures T from $T_{min}$ to $T_{max}$, the sensing element provides information about M and T in the form of two independently measured physical quantities $F_m$ and $F_t$. Depending on the sensing technique used they can be currents, voltages (in the case of piezoresistive, piezoelectric, Hall effect, etc. sensors), capacitances (capacitive MEMS sensors), frequencies or time and phase delays (sensors based on resonators and delay lines) and other quantities that can be easily converted into a digital format by electronic circuitry. In general, both $F_m$ and $F_t$ depend on M and T:

$$F_m = F_m(M,T), \quad (1)$$

$$F_t = F_t(M,T), \quad (2)$$

but their dependencies are different and these dependencies are established by sensor calibration within the temperature range of interest. This produces a calibration model, usually either in the form of look-up tables or in the form of polynomials approximating the actual calibration results. Combinations of both can also be used in order to reduce complexity of the calibration model. For example, if $F_m$ and $F_t$ depend on M linearly or piece-wise linearly, then the following model can be used:

$$F_m = \begin{cases} S_p(T)M + F_0(T), & M \geq 0 \\ S_n(T)M + F_0(T), & M < 0, \end{cases} \quad (3)$$

$$F_t = a_1 - a_2T - a_3M + a_4T^2 + a_5T^3, \quad (4)$$

where the sensitivities $S_{p,n}$ and the offset $F_0$ as functions of temperature can be represented by look-up tables in a number of discrete temperature calibration points covering the whole temperature range of interest:

| T | $S_p$ | $S_n$ | $F_0$ |
| --- | --- | --- | --- |
| $T_1$ | $S_{p1}$ | $S_{n1}$ | $F_{01}$ |
| $T_2$ | $S_{p2}$ | $S_{n2}$ | $F_{02}$ |
| ... | ... | ... | ... |
| $T_n$ | $S_{pn}$ | $S_{nn}$ | $F_{0n}$ |

A practical number of temperature calibration points can be from 10 to 5 for a typical automotive temperature range from −40° C. to +125° C. (it depends on a character of temperature variation of $S_{p,n}$ and $F_0$). If needed the look-up tables can be expanded on a larger number of points with a smaller temperature step by means of interpolation.

After developing the calibration model, the temperature-compensated value of M, as well as the temperature T, can be found from the sensor readings $F_m$ and $F_t$ by solving simultaneous equations Eqs. (1) and (2) or Eqs. (3) and (4) in the microprocessor.

Any individual physical sensor is fully characterised by a set of calibration parameters, for instance, polynomial coefficients $a_{1-5}$ and values in the look-up tables $S_{p1-n}$, $S_{n1-n}$, $F_{01-n}$.

This prior art approach is fine in theory but has its practical limitations. Individual sensors slightly differ from each other because of fabrication tolerances so that the individual calibration parameters also differ from each other. If the difference is small all the sensors can be described by the same generic calibration parameters $a_{1-5}$, $S_{p1-n}$, $S_{n1-n}$, $F_{01-n}$ that can be found as an average of the individual calibration parameters. In this case replacing of the actual individual calibration parameters by the generic ones for a particular sensor does not cause unacceptably large additional errors in the measured value of M. In practice, then, only a first batch of sensors (sufficiently large to be statistically representative) needs to be calibrated within the entire temperature range from $T_{min}$ to $T_{max}$ in order to find generic calibration parameters. The rest of sensors can be supplied without their calibration just relying on high repeatability of the manufacturing process. This is a standard approach allowing considerable reduction of the sensor cost by excluding a calibration cost from it.

Very often, however, variations in the sensor characteristics are too large to be able to use a single set of generic calibration parameters for all sensors without calibrating them. An example of this situation is demonstrated in FIG. 1, which shows errors in measuring engine output torque by 27 SAW resonant sensors installed on flexplates in the case if their individual calibration parameters are replaced by the generic ones. The curves are plotted against temperature for the measured torque value M=800 Nm, and show that the maximum error exceeds 100% of reading which is obviously unacceptable. In this case the prior art approach is to produce an individual calibration of each sensor within the entire temperature range. Bearing in mind that it needs to be done in relatively large number of temperature points, this process considerably increases the sensor cost. It may even be not feasible in some cases, for instance, if the sensor is installed on a large metal part and needs to be calibrated together with this part. In this case it may take 1-3 hours in order to reach a steady state at each temperature point.

SUMMARY OF THE INVENTION

The aim of the invented method is therefore to reduce considerably time and cost of individual calibration of the sensors with a large spread of characteristics by means of reduction of the number of temperature calibration points down to one or two.

According to the present invention there is provided a method of calibrating an individual sensor whose output varies non-linearly with at least one measured quantity and at least one operating condition, comprising the steps of: producing a generic calibration surface of a plurality of generic calibration curves for the variation of the sensor readings with the at least one measured quantity across the require operating range for the at least one operating condition for the particular sensor type of said individual sensor by calibrating a sufficiently large number of sensors at a large number of operating conditions and averaging the calibration data obtained; taking individual calibration measurements for a number of different values of the measured quantity for the individual sensor at just a small number of discrete values for the at least one operating condition which fall within the full range of operating values for the at least one operating condition for which the sensor is to be calibrated; and using said individual calibration readings to map the generic calibration curves or calibration surface to the in order to fit it to the individual sensor.

A method in accordance with the present invention has the advantage that it enables accurate calibration information to be produced for individual sensors having a large spread of characteristics in a time efficient and therefore cost effective manner.

Preferably, the measured quantity is torque and the operating condition is temperature, calibration reading for the individual sensor being taken at a small number of different temperatures, in particular at just two temperatures, for each temperature calibration readings being taken at a number of different torques. This has the advantage that the complexity of the calibration procedure is reduced since the number of temperature changes required, which is the time consuming part of the procedure, is reduced.

In the first stage, a sufficiently large number of sensors are calibrated at a sufficiently large number of operating conditions in order to produce effective generic calibration curves/surfaces establishing the non-linear dependence for the two sensor outputs ($F_m$ and $F_t$). Note that separate calibration curves/surface will be derived for the two sensor outputs—$F_m$ and $F_t$. Mapping functions are then used to map the generic calibration data to coincide with the actual individual readings taken for the individual sensor, and the fitted calibration curves/surface is then used as the correct calibration curve for the individual sensor.

Preferably, the step of producing generic calibration curves for the particular sensor type comprises producing detailed calibration curves for a sample number of sensors, e.g. 100, of the particular sensor type within the full operating range for the at least one operating condition, and then calculating average curves or calibration surface from the calibration curves obtained for the sample number of sensors, said average curves/surface being used as the generic calibration curves/surface.

In one embodiment, the at least one operating condition is a single operating condition, in particular temperature, both the measurements for generating the generic calibration curves as well as the calibration readings for the individual sensor being taken at discrete temperatures covering the full temperature operating range of the sensor type. It is, however, also possible to apply the method of the present invention to obtain calibration data for more than one operating parameter which impacts on the sensor readings in a manner which it is preferred to avoid.

In one embodiment, no more than three sets of calibration readings are taken for the individual sensor, each set of readings being taken at one value of the operating condition, the values of the operating condition advantageously spread across the operating range of the sensor, and in particular including one at room (ambient) value, such as ambient temperature, the latter having the particular advantage that minimal heating or cooling of the sensor will be required to take die ambient reading, hence speeding up the process. It has been found to be particularly effective to take just two sets of calibration readings for the individual sensor, each set comprising measured at 3 different values of the measured quantity, by which a good compromise is achieved between time taken to calibrate and accuracy. Applying the method with just a single calibration reading has also been found to produce acceptable results.

In the case of a single set of calibration reading being taken for the individual sensor, the generic calibration curves are mapped to the single calibration reading of the individual sensor by translating the generic calibration curves, effectively performing a zeroing function. In the case of two sets of calibration readings being taken, translation is again carried out as a zeroing function followed by a scaling of the curves by adjustment of the linear slope element of the generic curves/data, that is the term in the polynomial equation defining the calibrations curves that linearly depends on the operating condition (such as temperature).

BRIEF DESCRIPTION OF THE DRAWINGS

In order that the invention may be well understood, there will now be described an embodiment thereof, given by way of example, reference being made to the accompanying drawings, in which.

DETAILED DESCRIPTION OF THE PREFERRED EMBODIMENTS

Figure 1:
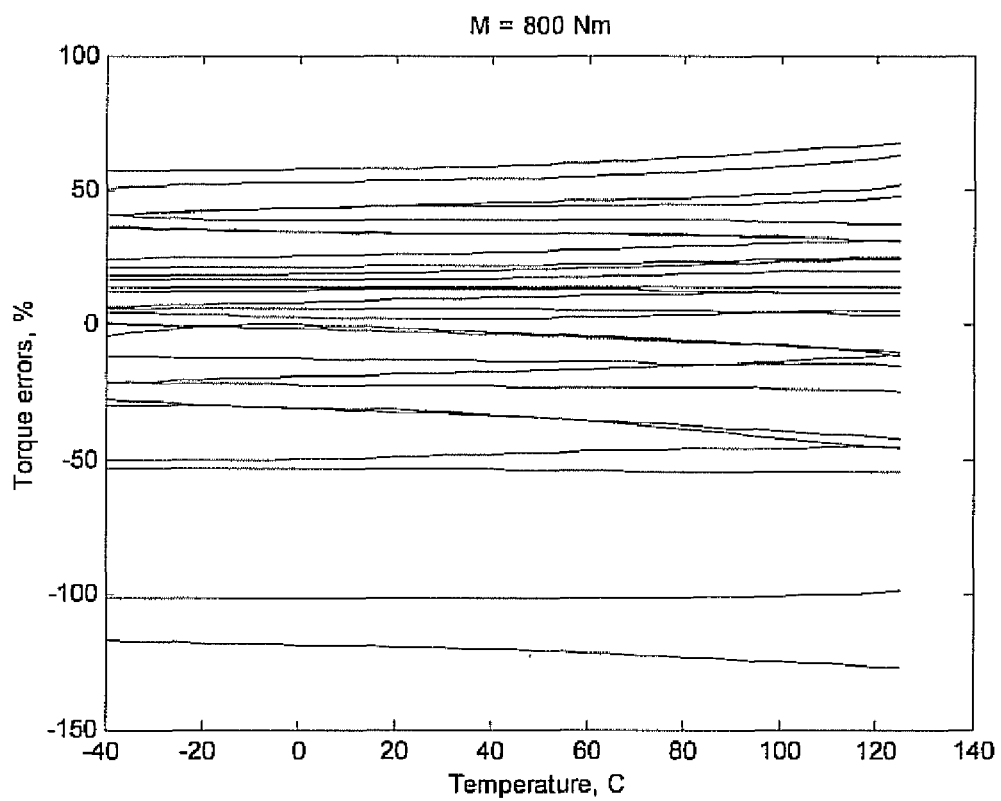
FIG. 1 is a graph illustrating the error in the measurement obtained from a number of SAW sensors using temperature compensation calibration according to the prior art practice, i.e. when the generic calibration data are applied to the individual sensors.

The steps of a calibration method embodying the invention are described hereinafter in connection with temperature calibration of a SAW based sensor, although it will be understood that the method can also be used for calibrating other parameters effecting readings from a sensor and/or other types of sensor.

After developing a high-volume fabrication process for a particular type of sensor the sensor manufacturer produces and calibrates the first batch of sensors (say, 100 devices to be statistically representative) within the full range of temperatures from $T_{min}$ to $T_{max}$ in a sufficiently large number of temperature intervals (typically 5 to 10 discrete points).

This is achieved in practice by heating up or cooling down each individual sensor to a required calibration temperature point $T_i$ (i=1 ... N) and taking the two readings, $F_m$ and $F_t$, at a number of predefined values of measured torque value M. In the case of the model described by Eqs. (3) and (4), only three values can be used, negative $M_n$, 0, and positive $M_p$, in order to find $a_3$, the sensitivities $S_{p,n}$ and the offset $F_0$ at each calibration temperature point. The rest of the coefficients $a_{1-5}$ are calculated on the basis of least mean square errors to fit the temperature calibration curves.

The calibration data $a_{1-5}$, $S_{p,n}(T)$, $F_0(T)$ is calculated for each sensor from the batch and then a generic set of calibration parameters $a_{1-5}$, $S_{p,n}(T)$, and $F_0(T)$ is found by means of averaging. This step is similar to the standard approach described above. It should be noted here that the set of calibration parameters and the calibration model for some sensors might differ from those described by Eqs. (3) and (4) above, which are given merely as an example. However, the skilled person will know or being able to derive the required equations for any sensor using his common knowledge and without inventive thought, and hence he does not need to be taught those equations in order to put the subject invention into practice.

Once the calibration curves have been formulated, each production sensor is calibrated only at one or two temperature points, depending on the spread of the sensor characteristics and acceptable calibration errors. For instance, the single temperature calibration point can be room temperature $T_0=20°$ C. One of the two calibration points can also be room temperature $T_0=20°$ C. and the second point can be an engine operating temperature $T_c=90°$ C. if the sensor is aimed at engine output torque measurement. Selection of the calibration temperatures $T_0$ and $T_c$ depends on the application, the temperature range and the spread of the sensor characteristics. It is, though preferable that the two values are spread across the operating temperature range of the sensor, or, in the case of a single temperature reading, is not close to either end of the operating range of the sensor.

At each temperature, a number of readings are taken at a number of different toque values, variation of the torque applied to the sensor being easier to implement than varying the temperature.

Generic calibration parameters $a_{1-5}$, $S_{p,n}(T)$, and $F_0(T)$ are then corrected for this particular sensor on the basis of the obtained information. Correction method is designed in such a way that it provides zero calibration errors either at one temperature $T_0$ or at two temperatures, $T_0$ and $T_c$.

As an example, consider the correction method for a sensor described by Eqs. (3) and (4) in the case of one-point calibration. In this case, the individual calibration data are:

$$F_{00}=F_m(0,T_0), \quad (5)$$

$$F_{t0}=F_t(0,T_0), \quad (6)$$

$$S_{p,n0}=[F_m(M_{p,n},T_0)-F_m(0,T_0)]/M_{p,n}, \quad (7)$$

$$S_{t0}=\{[F_t(M_p,T_0)-F_t(0,T_0)]/M_p+[F_t(M_n,T_0)-F_t(0,T_0)]/M_n\}/2, \quad (8)$$

The correction of the generic calibration parameters is performed in the following way. The individual calibration coefficients $$a_3'=-S_{t0}, \quad (9)$$

$$a_1'=F_{t0}+a_2T_0-a_4T_0^2-a_5T_0^3 \quad (10)$$

replace the relevant generic coefficients and each value in the generic look-up tables is re-calculated according to the equations, $$F_0'(T)=F_0(T)+F_{00}-F_0(T_0), \quad (11)$$

$$S_{p,n}'(T)=S_{p,n}(T)+S_{p,n0}-S_{p,n}(T_0). \quad (12)$$

Figure 2:
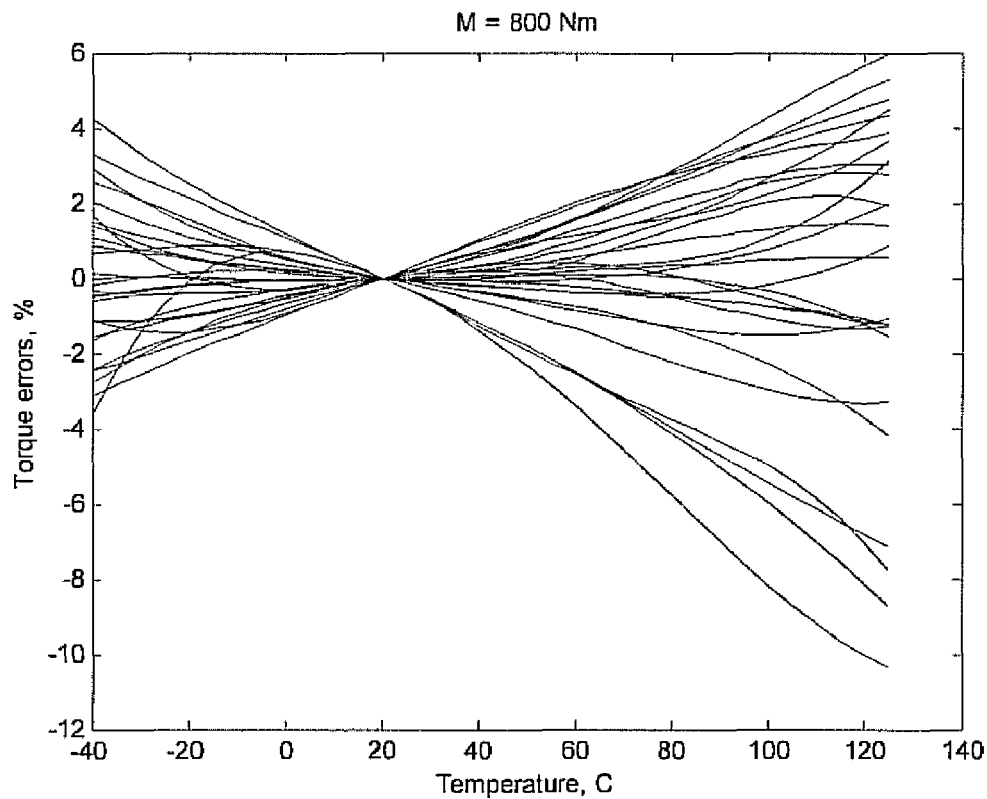
FIG. 2 is a graph illustrating the error in the measurement obtained from a number of SAW sensors using temperature compensation calibration according to the present invention taking calibration measurement for each sensor just at a single temperature.

Coming back to the example of the SAW flexplate torque sensor shown in FIG. 1, the correction procedure applied after one-point calibration allows achieving a considerable reduction of the errors in comparison with the case when the individual calibration is not performed at all. FIG. 2 shows the errors in measuring torque against temperature in the case of one-point calibration at $T_0=20°$ C. and the measured torque M=800 Nm. Maximum error is now reduced to 10% of reading. It may be acceptable for some applications but if it is still too large then a two-point calibration can be used.

Consider now the correction method for the sensor described by Eqs. (3) and (4) in the case of two-point calibration. Apart from the data described by Eqs. (5)-(8), the individual calibration data includes offsets and torque sensitivities measured at the second calibration point $T_c$:

$$F_{0c}=F_m(0,T_c), \quad (13)$$

$$F_{tc}=F_t(0,T_c), \quad (14)$$

$$S_{p,nc}=[F_m(M_{p,n},T_c)-F_m(0,T_c)]/M_{p,n}, \quad (15)$$

$$S_{tc}=\{[F_t(M_p,T_c)-F_t(0,T_c)]/M_p+[F_t(M_n,T_c)-F_t(0,T_c)]/M_n\}/2. \quad (16)$$

As a result of correction of the generic calibration data the new individual calibration coefficients are as follows:

$$a_3'=-(S_{t,0}+S_{tc})/2, \quad (17)$$

$$a_2'=[F_{t0}-F_{tc}+a_4(T_c^2-T_0^2)+a_5(T_c^3-T_0^3)]/(T_c-T_0), \quad (18)$$

$$a_1'=F_{tc}+a_2'T_c-a_4T_c^2-a_5T_c^3. \quad (19)$$

The corrected look-up tables are described by the equations:

$$F_0'(T)=F_0(T)+-F_{00}-F_0(T_0)+[F_{0c}-F_0(T_c)-F_{00}+F_0(T_0)](T-T_0)/(T_c-T_0), \quad (20)$$

$$C_{p,n}'(T)=C_{p,n}(T)+C_{p,n0}-C_{p,n}(T_0)+[C_{p,nc}-C_{p,n0}+C_{p,n}(T_0)](T-T_0)/(T_c-T_0). \quad (21)$$

Figure 3:
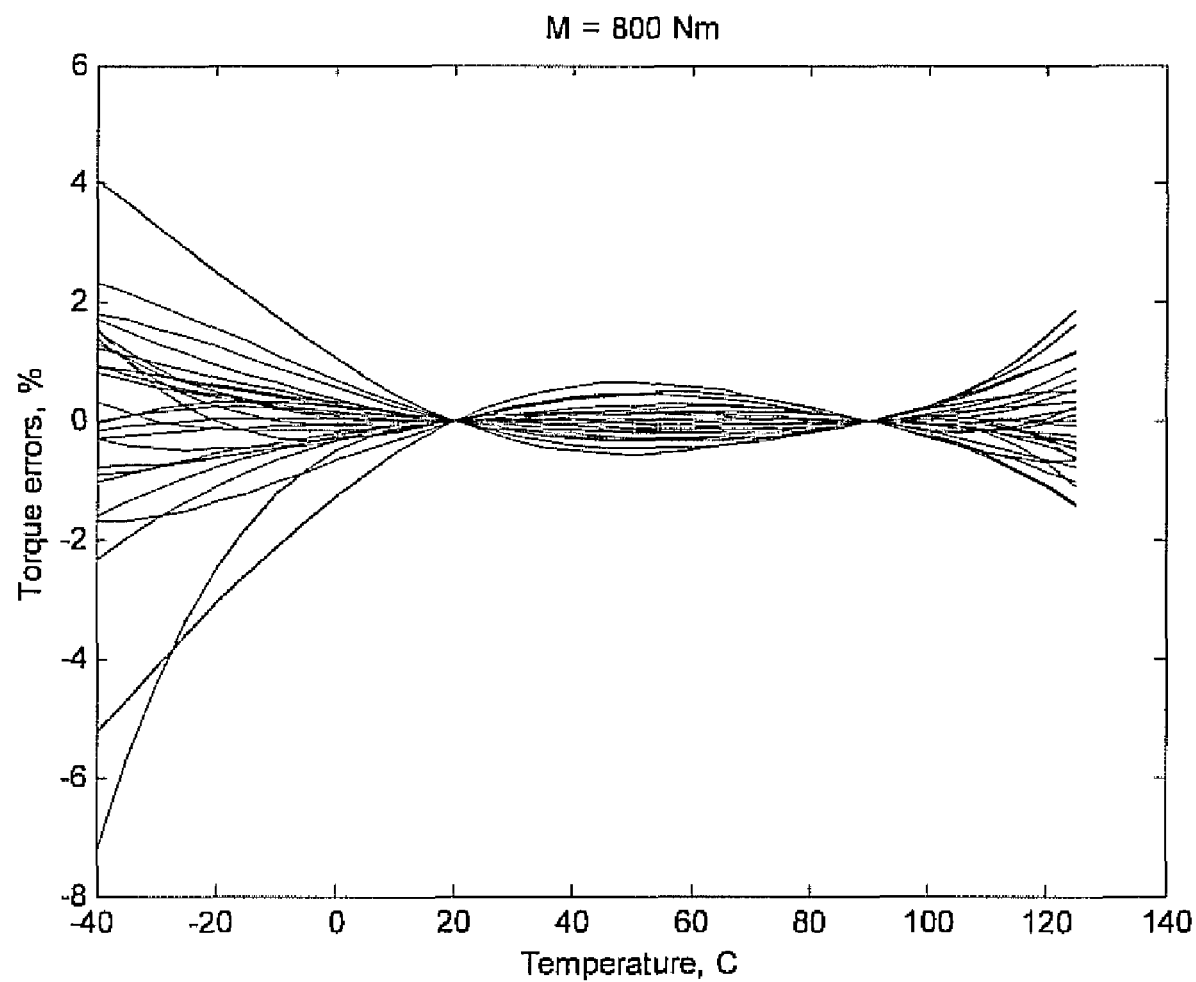
FIG. 3 is a graph illustrating the error in the measurement obtained from a number of SAW sensors using temperature compensation calibration according to the present invention using two-point calibration at 20 degrees and 90 degrees.

FIG. 3 illustrates reduction of the torque measurement errors achieved in the case of two-point calibration for $T_0=20°$ C. and $T_c=90°$ C. and the measured torque value of 800 Nm. One can see that a further considerable improvement of the sensor accuracy can be achieved in comparison with one-point calibration within a wide temperature range.

If the two-point calibration is performed by the sensor manufacturer then it allows reduction of the calibration time at least by a factor of four. If the two-point calibration is performed by the OEM during end-of-line tests then time and energy saving will be even larger.

The particular implementations of the correction methods for the generic calibration parameters described by Eqs. (9)-(12) for one-point calibration and by Eqs. (17)-(21) for two-point calibration are presented here just as examples. The methods can be easily modified to suit any calibration model, and it is the overall approach of fitting the generic data to the measured values for a particular sensor which is essential to the invention. Formulation of calibration equations for different sensors corresponding with those set out above will be within the practical skill of skilled reader and will not, therefore, be taught any further herein. The main requirement for the calibration equations is to adjust the calibration parameters in such a way that the calibration errors for an individual sensor become zero at the temperatures where calibration is performed.

A further reduction of the errors can be achieved if a third temperature calibration point is added, that is a third discrete calibration reading is taken for each individual sensor so as to further improve the accuracy of the fit of the calibration curve against the actual temperature response of the sensor. Again, the individual calibration parameters are obtained in this case by correcting the generic calibration parameters on the basis of the calibration data in such a way that the calibration errors turn into zero at three temperatures where calibration was performed.

What is claimed is:

1. A method of calibrating an individual sensor of a particular sensor type whose output varies non-linearly with at least one measured quantity and at least one operating condition, comprising the steps of:
   a) producing a set of calibration curves for a sample sensor of the particular sensor type, each curve showing the variation of the sample sensor output with the at least one measured quantity at a different value of the operating condition for the particular sensor type of said individual sensor, said set of curves covering the required operating range for the particular sensor type;
   b) repeating step (a) a plurality of times with a plurality of different sample sensors of the particular sensor type so as to produce a set of calibration curves for each sample sensor;
   c) averaging said the plurality of sets of calibration curves of the plurality of sensors derived from step (b) and using the result to produce a generic calibration surface for the particular sensor type showing the variation of the sensor reading with the at least one measured quantity across the required operating range;
   d) taking individual calibration measurements for a number of different values of the measured quantity for the individual sensor at just a small number of discrete values for the at least one operating condition which fall within the full range of operating values for the at least one operating condition for which the sensor is to be calibrated; and
   e) using said individual calibration readings to map the generic calibration surface to the individual calibration measurements of the individual sensor in order to fit it to the individual sensor.

2. A method according to claim 1, wherein the output of the individual sensor type varies non-linearly with at least two measured quantities, steps (a) to (e) being carried out for each measured quantity so as to produce a generic calibration curve for each measured quantity which is mapped to the individual calibration measurements of the individual sensor for the associated measured quantity.

3. A method according to claim 1, wherein the measured quantity is torque and the operating condition is temperature, calibration reading for the individual sensor being taken at a small number of different temperatures, each temperature calibration readings being taken at a number of different torques.

4. A method according to claim 3, wherein said small number of different temperatures comprises two different temperatures.

5. A method according to claim 1, comprising the further step of generating mapping functions for the or each measured quantity for mapping the generic calibration data to coincide with individual calibration measurements of the individual sensor.

6. A method according to claim 1, wherein step (b) comprises repeating step (a) on a sample number of at least 100 sensors for the particular sensor type.

7. A method according to claim 1, wherein the at least one operating condition is a single operating condition, in particular temperature, both the measurements for generating the generic calibration curves as well as the calibration readings for the individual sensor being taken at discrete temperatures covering the full temperature operating range of the sensor type.

8. A method according to claim 1, wherein no more than three sets of calibration readings are taken for the individual sensor, each set of readings being taken at one value of the operating condition.

9. A method according to claim 8, wherein the values of the operating condition are spread across the operating range of the sensor.

10. A method according to claim 9, wherein the values of the operating condition include one at room (ambient) value.

11. A method according to claim 1, wherein just two sets of calibration readings are taken for the individual sensor, each set comprising measurements at 3 different values of the measured quantity.

12. A method according to claim 1 the generic calibration surface is mapped to the calibration readings by translation as a zeroing function followed by a scaling of the data by adjustment of the linear slope element of the generic curves/data, that is the term in the polynomial equation defining the calibrations curves that linearly depends on temperature.

13. A method according to claim 1, wherein just a single set of calibration readings are taken for the individual sensor, the generic calibration data being mapped to the calibration reading of the individual sensor by translating the generic calibration surface, effectively performing a zeroing function.

* * * * *